US012631628B2

(12) United States Patent     (10) Patent No.: US 12,631,628 B2

Goun et al.     (45) Date of Patent: May 19, 2026

(54) POSITIONALLY PRECISE FUNCTIONALIZATION OF SHALLOW LUMINESCENT CENTERS THROUGH FORSTER RESONANT ENERGY TRANSFER (FRET) DRIVEN SURFACE PHOTOCHEMISTRY

(71) Applicant: The Trustees of Princeton University, Princeton, NJ (US)

(72) Inventors: Alexei Goun, Plainsboro, NJ (US); Herschel Rabitz, Lawrenceville, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 475 days.

(21) Appl. No.: 18/143,726

(22) Filed: May 5, 2023

(65) Prior Publication Data

US 2023/0358734 A1    Nov. 9, 2023

Related U.S. Application Data

(60) Provisional application No. 63/338,607, filed on May 5, 2022.

(51) Int. Cl.
*G01N 21/64*      (2006.01)
*B01L 3/00*      (2006.01)
(Continued)

(52) U.S. Cl.
CPC .. *G01N 33/54373* (2013.01); *B01L 3/502707* (2013.01); *B01L 3/502761* (2013.01);
(Continued)

(58) Field of Classification Search
CPC ......... G01N 33/54373; B01L 3/502707; B01L 3/502761; B01L 2200/0652;
(Continued)

(56) References Cited

U.S. PATENT DOCUMENTS

2014/0191139 A1* 7/2014 Englund ............ G01N 21/6428
                 536/23.1
2016/0161429 A1* 6/2016 Englund ............ G01N 21/6402
                 324/304

\* cited by examiner

*Primary Examiner* — Jennifer Wecker
*Assistant Examiner* — Oyeleye Alexander Alabi
(74) *Attorney, Agent, or Firm* — Meagher, Emanuel, Laks, Goldberg & Liao, LLP

(57) ABSTRACT

Disclosed is an enabling process for high throughput manufacturing of large variety of chemical and biological sensors that utilize well-developed spin-based sensing of analyte binding. A method for producing a nanometer scale analyte specific sensor may be provided, that includes providing a first material (such as a diamond) having a luminescent center (such as an NV center) within predetermined distance (such as 2-5 nm) of a first surface, where the luminescent center configured to emit within an optical emission range, providing photochemically active molecules (such as molecules with a photo-uncaging protective group) where an optical absorption range of the photochemically active molecules at least partially overlaps the optical emission range, coating the first surface of the first material with the photochemically active molecules, and may include placement of the photochemically active surface molecule within a distance smaller than the Forster Resonant Excitation Transfer (i.e., 2-10 nm) from a luminescent center.

6 Claims, 11 Drawing Sheets

(51) Int. Cl.

| | |
|---|---|
| *B41J 2/14* | (2006.01) |
| *B82Y 5/00* | (2011.01) |
| *B82Y 30/00* | (2011.01) |
| *B82Y 40/00* | (2011.01) |
| *C07F 5/02* | (2006.01) |
| *C09B 57/00* | (2006.01) |
| *C09K 11/06* | (2006.01) |
| *C12Q 1/6818* | (2018.01) |
| *G01M 3/20* | (2006.01) |
| *G01N 1/30* | (2006.01) |
| *G01N 15/10* | (2024.01) |
| *G01N 15/1429* | (2024.01) |
| *G01N 27/626* | (2021.01) |
| *G01N 31/22* | (2006.01) |
| *G01N 33/483* | (2006.01) |
| *G01N 33/543* | (2006.01) |
| *G01N 33/58* | (2006.01) |
| *G01N 33/68* | (2006.01) |
| *C08J 7/04* | (2020.01) |

(52) U.S. Cl.
CPC ........ *B41J 2/14153* (2013.01); *C12Q 1/6818* (2013.01); *G01M 3/20* (2013.01); *B01L 2200/0652* (2013.01); *B01L 2300/0654* (2013.01); *C08J 7/04* (2013.01); *C12Q 2563/103* (2013.01)

(58) Field of Classification Search
CPC .......... B01L 2300/0654; B41J 2/14153; C12Q 1/6818; C12Q 2563/103; G01M 3/20; C08J 7/04
See application file for complete search history.

· — · · — · · —  a=4nm

············· a=3nm

— — — — — a=2nm

———————— True Rate = False Rate

· — · · — · · —  d=1nm

············· d=3nm

— — — — — d=5nm

———————— True Rate = False Rate

POSITIONALLY PRECISE FUNCTIONALIZATION OF SHALLOW LUMINESCENT CENTERS THROUGH FORSTER RESONANT ENERGY TRANSFER (FRET) DRIVEN SURFACE PHOTOCHEMISTRY

CROSS-REFERENCE TO RELATED APPLICATIONS

The present application claims priority to U.S. Provisional Patent Application 63/338,607, filed May 5, 2022, the contents of which are incorporated by reference herein in its entirety.

STATEMENT REGARDING FEDERALLY SPONSORED RESEARCH OR DEVELOPMENT

This invention was made with government support under Grant No. DE-FG02-02ER15344 awarded by the Department of Energy. The government has certain rights in the invention.

TECHNICAL FIELD

This present disclose is drawn to techniques and systems for detection assays using sensors with luminescent centers.

BACKGROUND

The recent rapid development of technology around single luminescent defects in solids opens a wide range of new capabilities in quantum information science, single-molecule structure, and dynamics analysis as well as allows the creation of a whole new range of biochemical detection platforms. The key to these capabilities is the long spin coherence time of luminescent paramagnetic centers such as Nitrogen-Vacancy (NV) sites in isotopically pure hosts (diamond). There is a wide variety of luminescent paramagnetic impurities NV centers in diamond, Magnesium in GaN, Phosphorous in Silicon, and other systems.

In the detection assays, the analyte molecule finds its selective binding partner, and the docking event is reported to the observer. This final reporting is typically done through optical emission detection, for example, the analyte molecule disturbing the excitation transfer process between donor and acceptor moieties and increasing the emission of the donor. Despite significant progress, optical emission-based detection essays face significant challenges as every new variant typically necessitates a novel molecular design that is expensive and time-consuming. Chromophores also have a strong tendency for photodegradation and many assay configurations are not scalable to simultaneous detection of a large number of biological and chemical targets. Thus, an essay that is label-free, operating on a broad range of chemical and biological targets (analytes) is highly desirable in health care, biomedical research, and defense applications.

BRIEF SUMMARY

To overcome deficiencies in the prior art, various devices, systems, and techniques may be provided.

In various aspects, a nanometer scale analyte-specific sensor may be provided. The sensor may include a first material (such as diamond) having a luminescent center (such as an NV center) within predetermined distance (such as within 2-5 nm) of a first surface coated with photochemically active molecules (such as molecules with photo-uncaging protective groups, e.g., such as those based on a near-IR cyanine dye), where the luminescent center configured to emit within an optical emission range, and an optical absorption range of the photochemically active molecules at least partially overlaps the optical emission range.

In various aspects, a system may be provided. The system may include a plurality of nanometer scale analyte specific sensors as disclosed herein, positioned within a fluid containing a molecule of interest. The system may also include a light source configured to illuminate the plurality of nanometer scale analyte specific sensors with at least one wavelength of light a luminescent center of each nanometer scale analyte specific sensors is capable of absorbing.

In various aspects, a kit may be provided. The kit may include a plurality of nanometer scale analyte specific sensors as disclosed herein, and may include a light source adapted to illuminate the plurality of nanometer scale analyte specific sensors with at least one wavelength of light a luminescent center of each nanometer scale analyte specific sensors is capable of absorbing.

In various aspects, a method for placing a chemical sensitive moiety in a close proximity of luminescent center may be provided. The method may include placing a nanometer scale analyte specific sensor as disclosed herein in a fluid containing a molecule of interest. The method may include exciting photoprotective groups of the photochemically active molecules, by photoexciting the luminescent center using at least one wavelength of light and causing the luminescent center to undergo Forster Resonant Excitation Transfer (FRET) to an optical chromophore of a photoprotective group. The method may include allowing the excited photoprotective groups to dissociate, leaving a functional group sterically available. The method may include attaching the molecule of interest to the sterically available functional group.

In various aspects, a method for producing a nanometer scale analyte specific sensor may be provided. The method may include providing a first material (such as diamond) having a luminescent center (such as an NV center) within predetermined distance (such as 2-5 nm) of a first surface, the luminescent center being configured to emit within an optical emission range. The method may include providing photochemically active molecules, where an optical absorption range of the photochemically active molecules at least partially overlaps the optical emission range. The method may include coating the first surface of the first material with the photochemically active molecules. The photochemically active molecules may include a photo-uncaging protective group (such as a group based on a near-IR cyanine dye). Coating the first surface may include depositing a monolayer containing the photo-uncaging protective group.

BRIEF DESCRIPTION OF FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

In FIG. 1A, the spin-labeled antagonist molecule is attached to the binding domain (e.g., an antibody), and no analyte molecule is

Figure 1A:
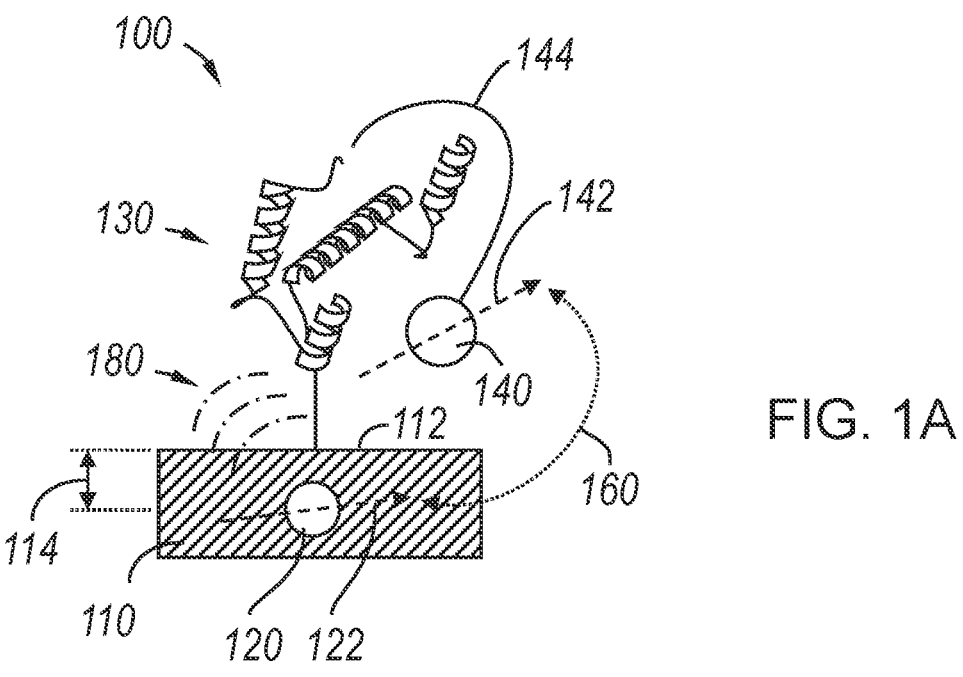
FIGS. 1A and 1B are illustrations of an Optically Detected-Electron Paramagnetic Resonance (OD-EPR) spin coupling-based ligand binding sensor.
Figure 1B:
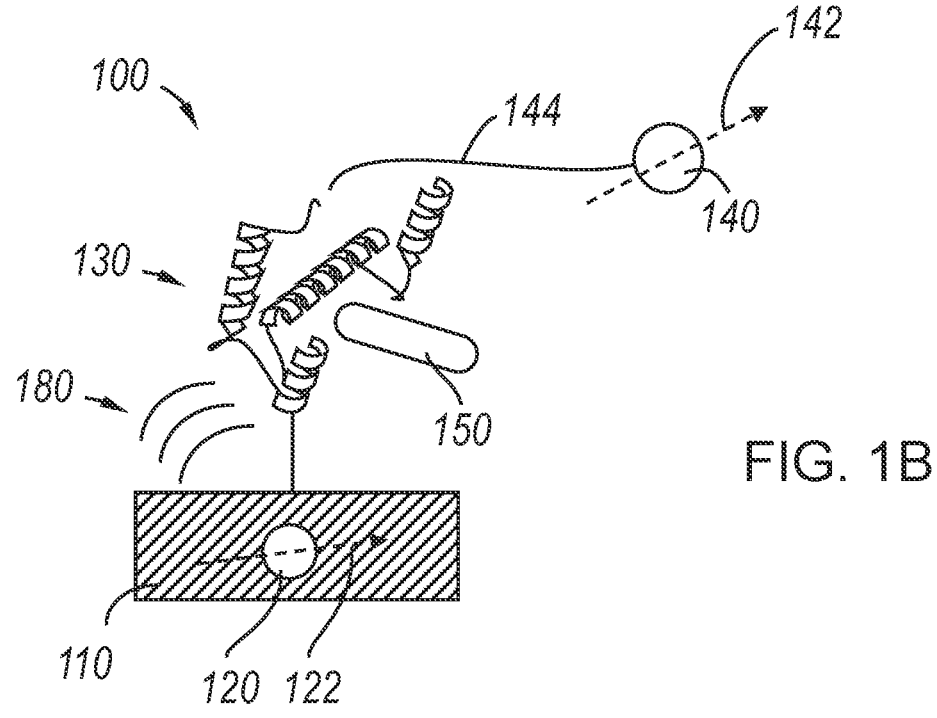

3 present. Due to the proximity of the spin-label to the NV center, there is a strong magnetic interaction, resulting in a large splitting in the EPR spectrum. In FIG. 1B, the detection system is shown after the attachment of the analyte molecule. The Analyte molecule displaces the spin-labeled Antagonist, significantly reducing the spin-spin magnetic interaction, and causing the reduction of the splitting in the EPR spectrum.

Figure 2:
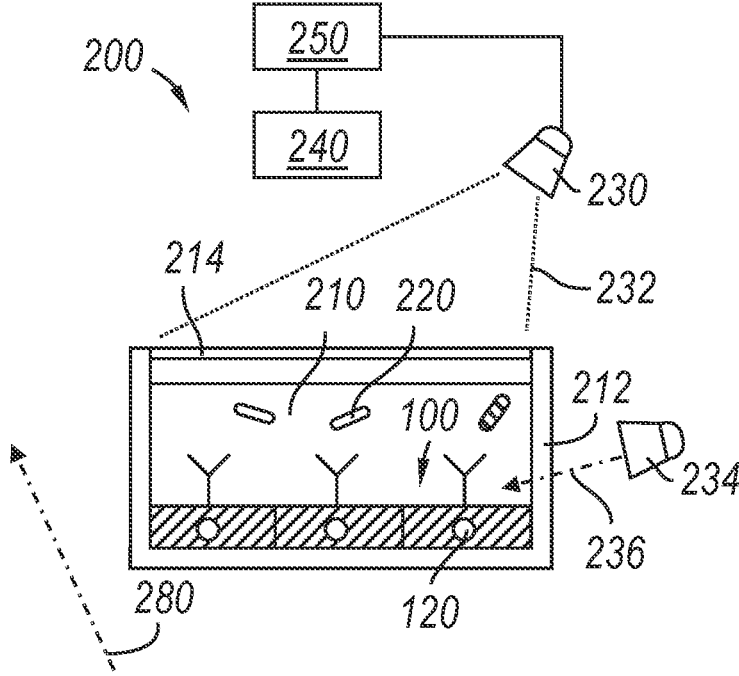

FIG. 2 is an illustration of a system.

Figure 3:
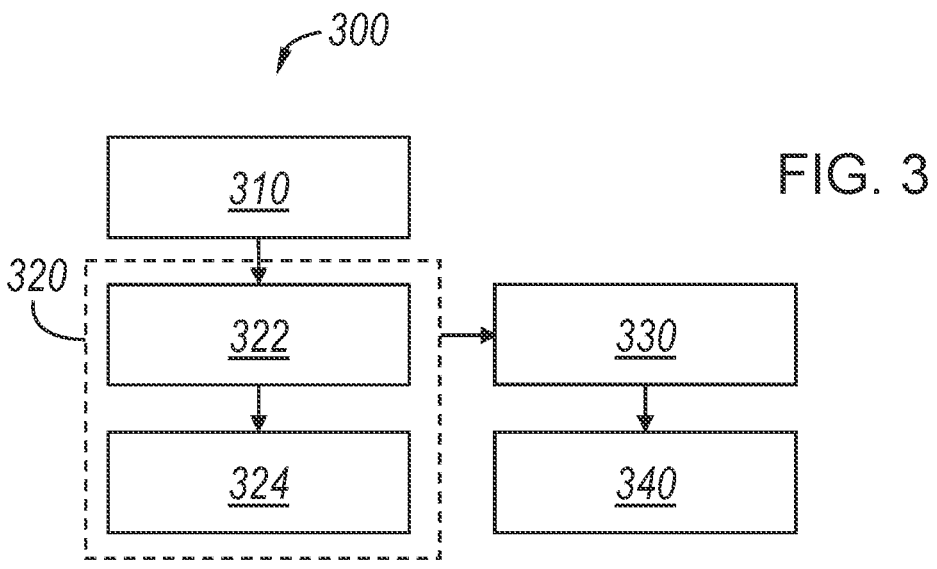

FIG. 3 is a simplified flowchart for a method of detecting an analyte.

Figure 4:
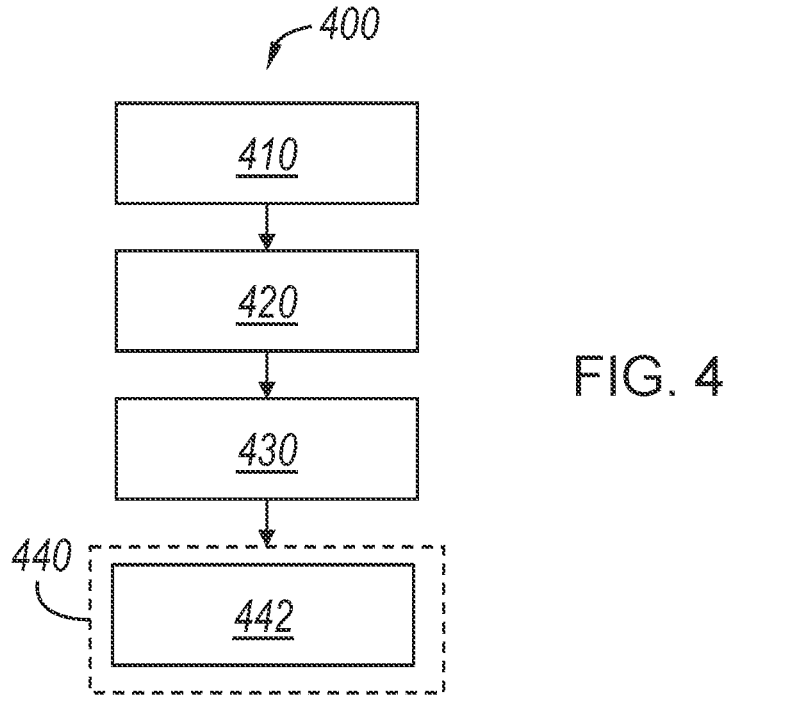

FIG. 4 is a simplified flowchart for a method of producing a nanometer scale analyte specific sensor.

FIG. 5A-5D show an illustrated version of a method for producing a nanometer scale analyte specific sensor.

Figure 5A:
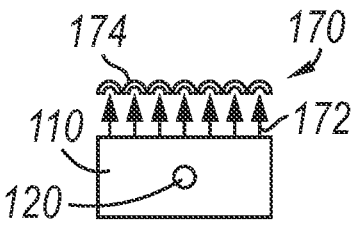
Figure 5B:
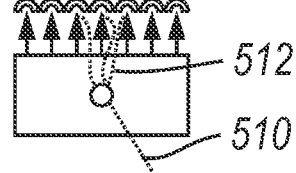
Figure 5C:
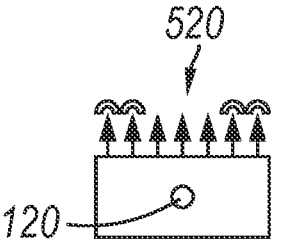
Figure 5D:
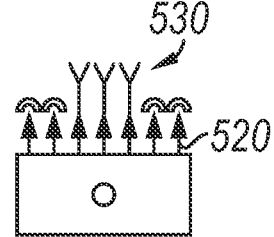
Figure 5E:
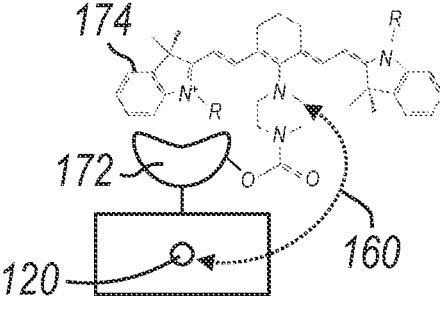
Figure 5F:
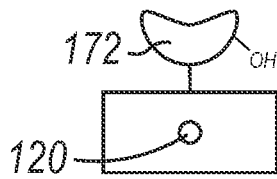

FIG. 5E-5F are illustrations showing use of a near-IR cyanine-based photoprotective group to control attachment to a function group, the functional group being in a cage (5E) and uncaged (5F) configuration.

Figure 6:
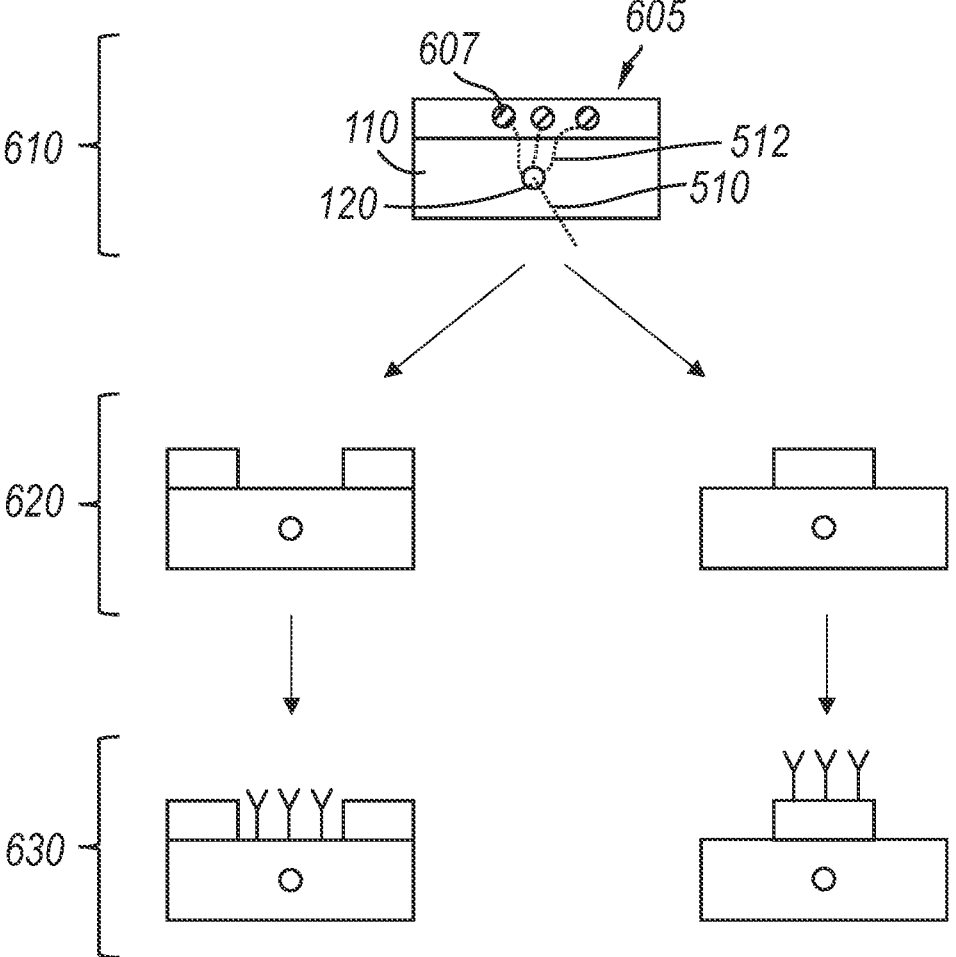

FIG. 6 shows an illustrated version of an alternate method for producing a nanometer scale analyte specific sensor.

Figure 7:
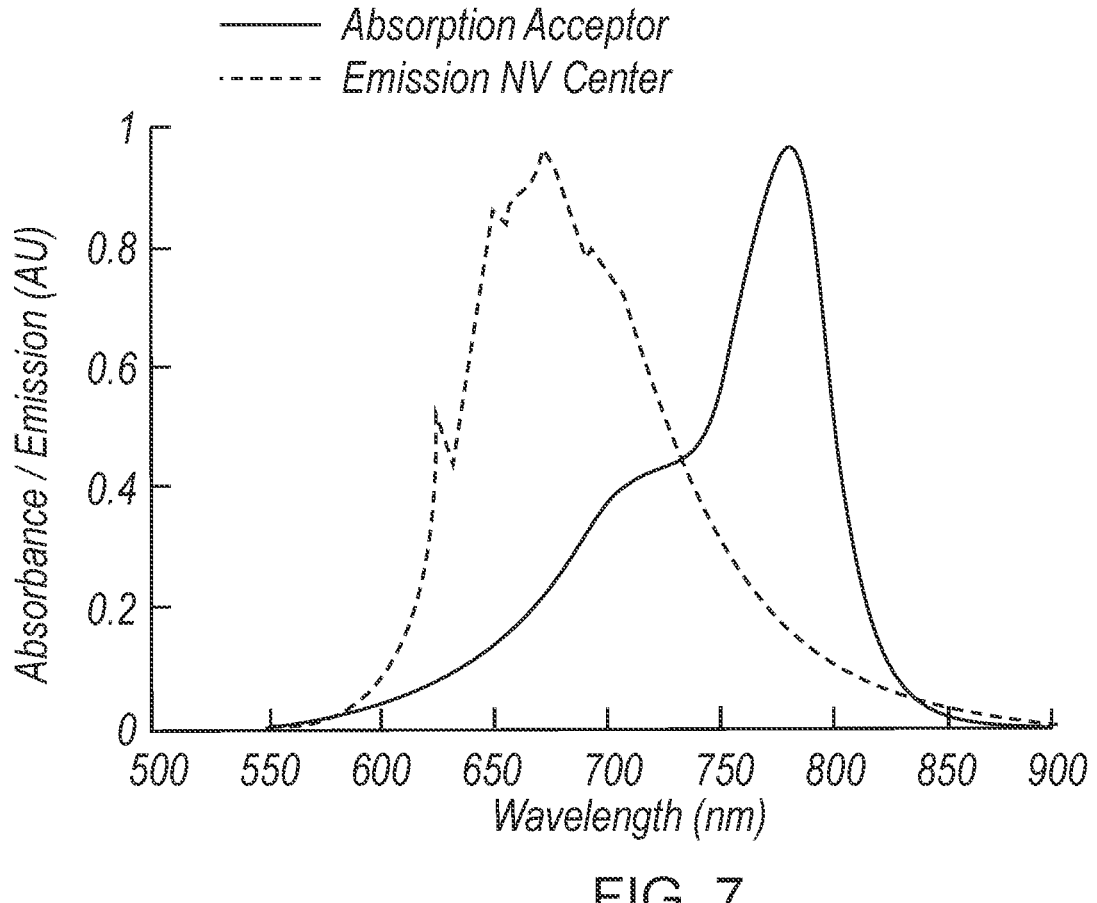

FIG. 7 is a graph showing the emission spectrum of the NV center (dashed lines) and the absorption spectrum of excitation acceptor (IR-780) (solid line). IR-780 is a light-sensitive component of a photo-uncaging, a protective group.

Figure 8:
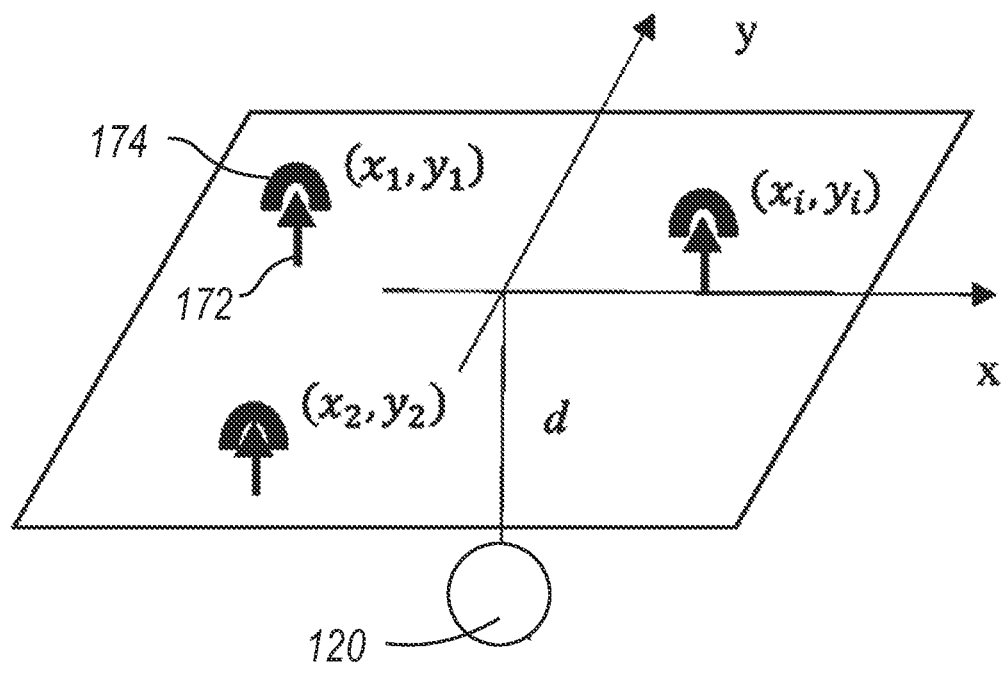

FIG. 8 is an illustration showing relative positions of an NV center and surface photo-uncaging groups, $(x_i, y_i)$ is the position of the i-th surface excitation accepting group, d is the deposition depth of the NV center.

Figures 9A, 9B, 9C:
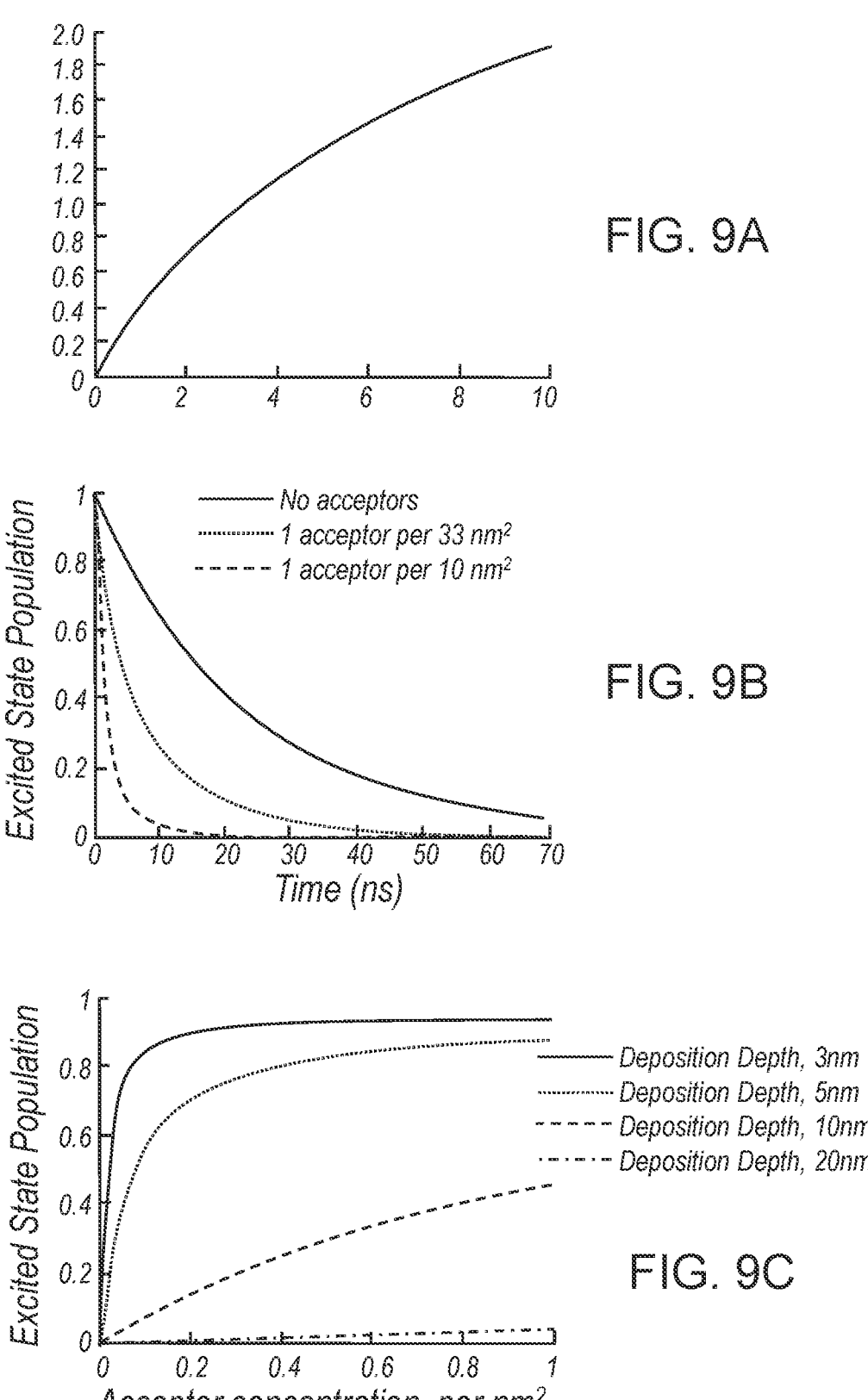

FIG. 9A is a graph showing the "form factor" of the excitation decay.

FIG. 9B is a graph showing the decay of the excited state of NV center.

FIG. 9C is a graph showing the probability of transfer to the surface group as a function of surface acceptor group concentration.

Figure 10A:
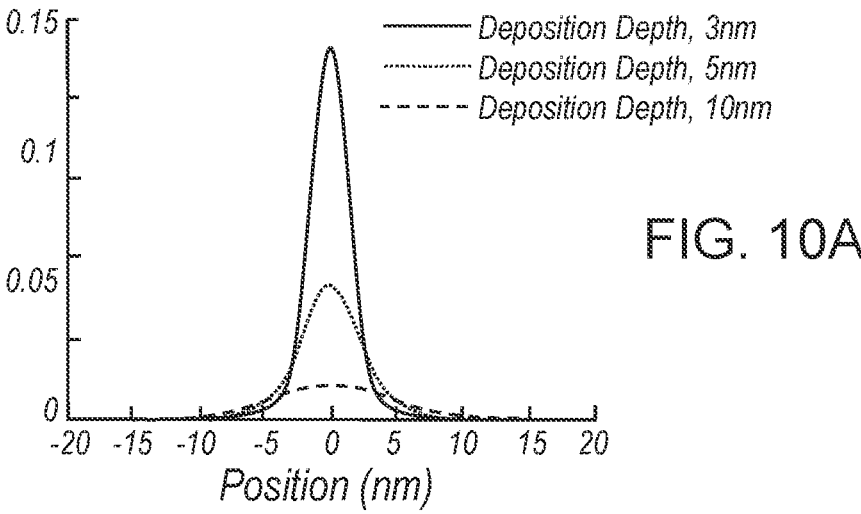

FIG. 10A is a graph showing the probability distribution of attachment sites for different depths of deposition of NV centers.

Figure 10B:
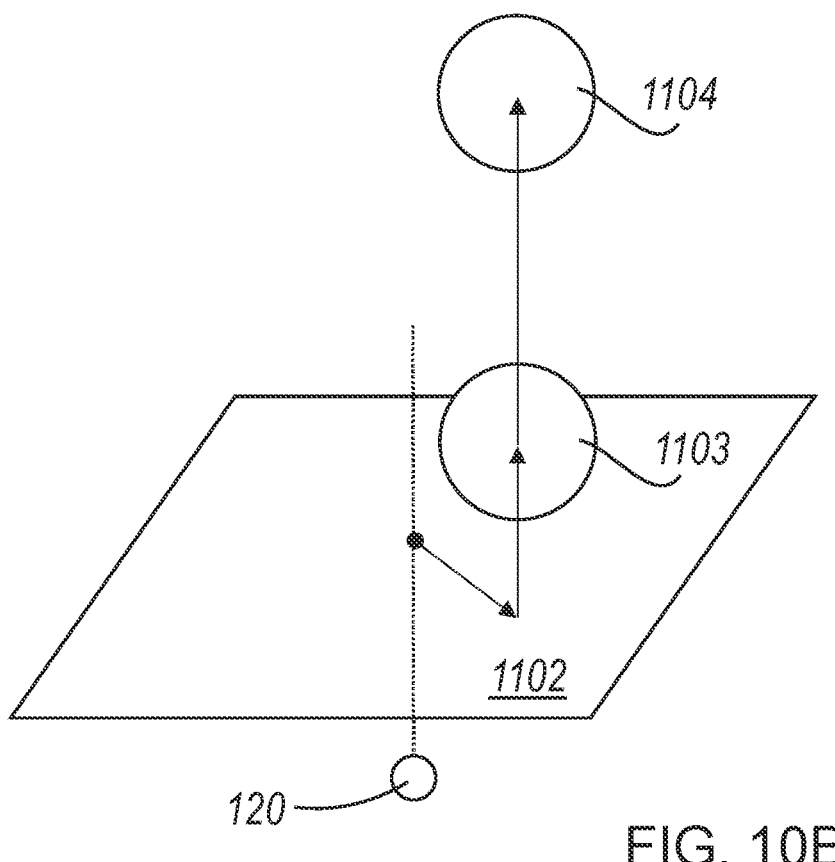

FIG. 10B is an illustration showing the mutual spatial configuration of an NV center (102) and the spin-label in the sensor analyte not-bound state (1104) and the analyte bound state (1103).

Figure 11A:
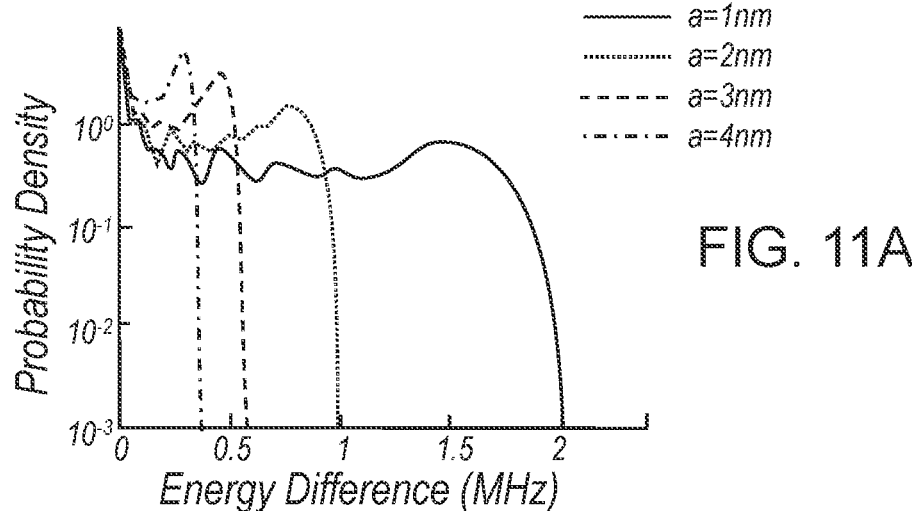
Figure 11B:
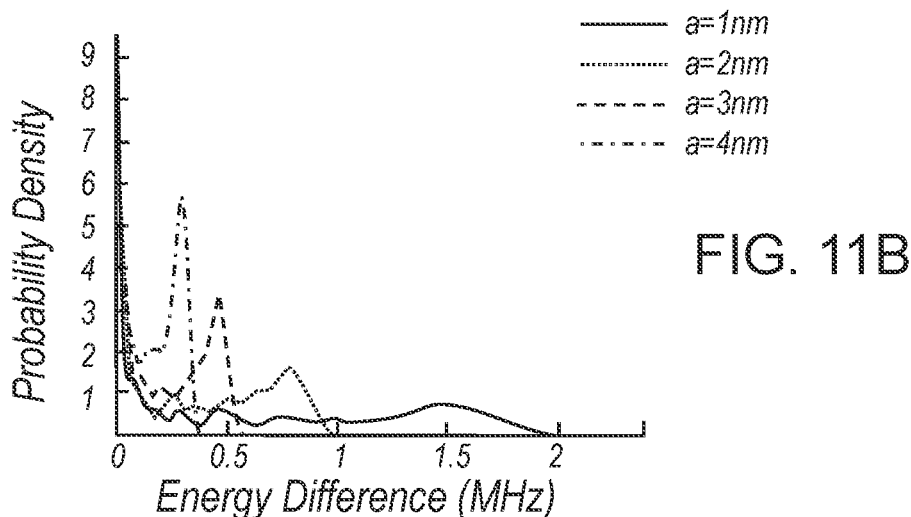

FIGS. 11A and 11B are graphs showing the probability distribution of the frequency separation in the optically detected ESR spectrum of the NV center coupled to the spin-label for different distances of spin-label above the diamond surface. The NV center deposition depth is assumed to be equal to 3 nm and the sphere of uncertainty is assumed to have a diameter of 0.5 nm.

Figure 12:
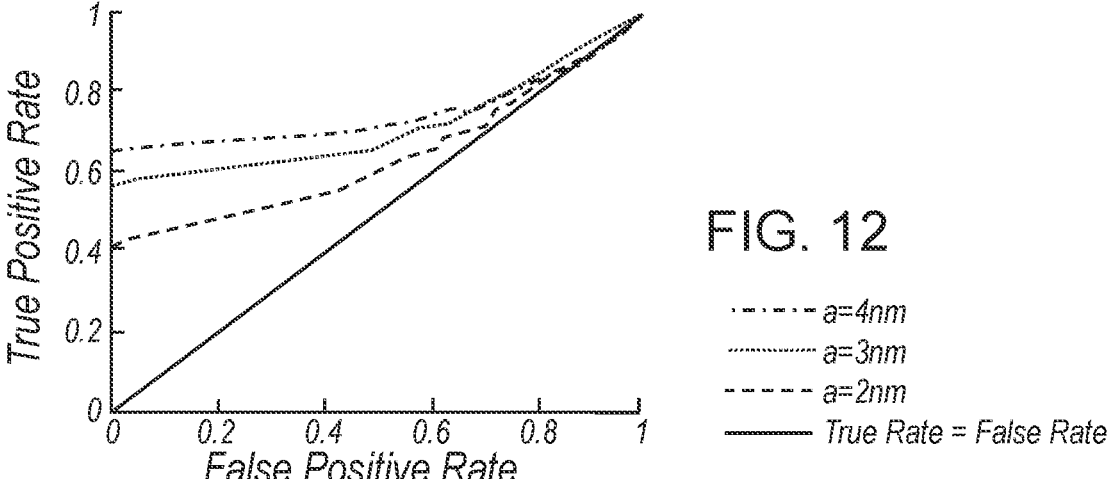

FIG. 12 is a graph showing the receiver operating curve (ROC) of the spin sensor-NV center for various positions (displacement of spin-label above the diamond surface) of the ON state. The position of the OFF state is 1 nm above the surface.

Figure 13:
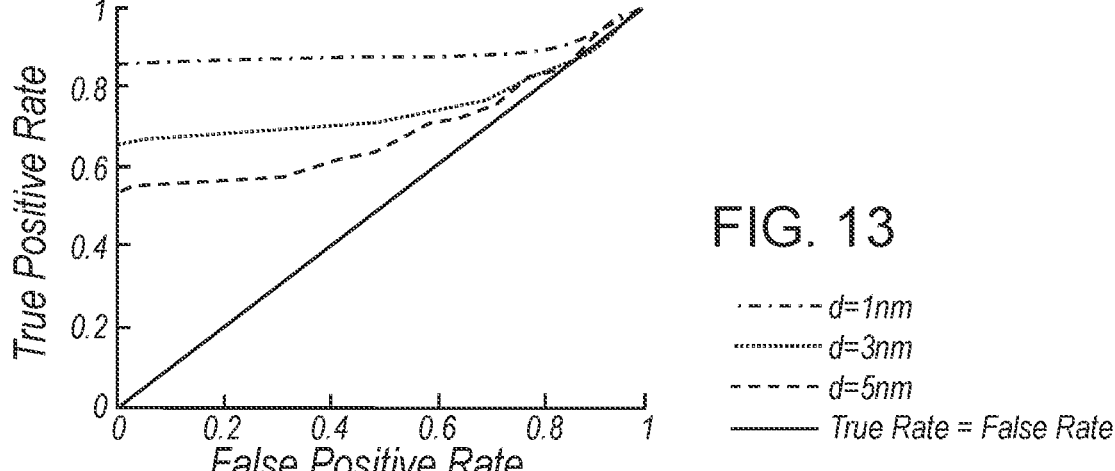

FIG. 13 is a graph showing receiver operating characteristic of the spin sensor—NV center for different deposition depths. The position of the OFF state is 1 nm above the surface, the position of the ON state is 1 nm above the surface, the diameter of uncertainty is 0.5 nm.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

Spin-based biological and chemical detection systems offer a novel, promising approach allowing highly integrated assays. The technique of spin labeling of proteins is well developed and allowed a broad range of measurements of proteins dynamics and structure. Spin-labeled antibodies are also regularly utilized in structural and dynamic measurements. The spin-label can be either covalently attached to the protein or form a thermodynamically stable complex. Detection of the single spin-label, attached to the surface of the protein with the help of the NV center was recently demonstrated.

The chemical and biological detection approach through the use of spin-labeled molecular sensors may be improved upon. The proposed operation of the spin-based molecular sensor is shown in FIGS. 1A and 1B.

The detector is represented by the isotopically pure CVD-grown diamond chip, with a single layer of NV-centers deposited in the vicinity of the surface using the delta-doping approach. The density of NV-centers in the layer is low enough to permit individual optical access and detection to individual centers. For the emission wavelength of 675 nm, the Abbe resolution limit) 172NA implies the possibility to integrate up to ~108 detection centers per $cm^2$ of the chip. Large separation between NV centers within the monolayer eliminates the broadening of spin resonance transition due to magnetic interactions among centers. Spin-based optical sensors are added to the chip through the route described in the next section. The liquid, containing the mixture of analytes is deposited on the surface of the chip with the help of microfluidic components. Analytes in the mixture interact with a surface-bound array of sensors and find the complementary targets through the diffusion-limited reaction.

The core detection technique is the Optically Detected-Electron Paramagnetic Resonance (OD-EPR). The emission of the NV center in diamond is dependent on its spin state, which allows measurement of the EPR spectrum of its environment through optical detection. The disclosed sensing system is composed of two components, the surface chemically/biologically sensing domain with spin-labeled antagonist molecule and the luminescent NV center that serves as a reporter for the spin state of the system. In this case, the sensing and optical reporting are separated, the sensing domain is not subject to photodegradation, and a broad range of sensing domains can be easily constructed. The attachment of the analyte molecule will cause a geometric change in the binding domain, affecting the coupling between the spin-labeled antagonist and the NV center.

The key to detection and in general quantum information processing capabilities is the long spin coherence time of NV centers. To ensure such a long time, the NV center must be placed sufficiently deep within the diamond, at the same time the center must be close enough to the surface to allow the interaction with external electron and nuclear spins. The ability to satisfy these conditions, together with a high degree of photostability gives NV centers their unique capability.

In various aspects, a nanometer scale analyte-specific sensor may be provided.

Referring to FIG. 1A, the sensor 100 may include a first material 110 having a luminescent center 120. The first material may be an appropriate material for such sensors, including diamond, such as an artificial diamond, silicon carbide, gallium nitride, aluminum nitride, or hexagonal-boron nitride. The luminescent center may be any appropriate center type, such as a nitrogen vacancy (NV) center, including neutral (NV$^0$) and negative (NV$^-$) centers. The luminescent center may be, or may also include, other types of centers as appropriate, such as a silicon vacancy (SiV) center, or a carbon anti site-vacancy pair (e.g., in silicon carbide).

The luminescent center may exhibit a spin in a first direction 122.

The luminescent center 120 should be within a predetermine distance 114 of a first surface 112 coated with photochemically active molecules 130, which may be an antibody. These photochemically active molecules may sometimes be referred to as the "binding domain" of the sensor. The photochemically active molecules should be selected to have an optical absorption range that at least partially overlaps the optical emission range of the luminescent center.

The photochemically active molecule may be a spin-labelled antibody. As used herein, the term "spin label" refers to an organic molecule possessing an unpaired electron, such as on a nitroxide NO, gadolinium, and the ability to bind to another molecule. Non-limiting examples of such antibodies include those described in, e.g., Galazzo, L., et al., "Spin-labeled nanobodies as protein conformational reporters for electron paramagnetic resonance in cellular membranes", PNAS 117(5) 2441-2448 (Jan. 21, 2020), Haugland, M. M., et al., "Tuning the properties of nitroxide spin labels for use in electron paramagnetic resonance spectroscopy through chemical modification of the nitroxide framework", Electron Paramagnetic Resonance V. 25 (Nov.

30, 2016), and Hsia, J. C., et al., "Spin-labeling as a general method in studying antibody active site", Archives of Biochemistry and Biophysics, vol. 129(1), p. 296-307 (1969), which are each incorporated by reference herein in their entirety.

The predetermined distance should be 2-30 nm, preferably 2-15 nm, more preferably 2-10 nm, and most preferable 2-5 nm. This depth can be tightly controlled withing the disclosed range using a delta-doping scheme. Spins at smaller deposition depths suffer from an increased rate of dephasing. Spins at large deposition depth do not couple efficiently to spins on the surface.

The photochemically active molecules preferably have photoprotective groups that can be excited. Specifically, they can be excited by photoexciting the luminescent center using a wavelength of light the center can absorb, and causing the luminescent center to undergo Forster Resonant Excitation Transfer (FRET) to an optical chromophore of a photoprotective group.

Non-limiting examples of chromophores, such as fluorophores, or "dyes", that may be used includes, e.g., IR-125 (Indocyanine Green) (Sodium 4-[(2E)-2-{(2E,4E,6E)-7-[1, 1-dimethyl-3-(4-sulfonatobutyl)-1H-benzo[e]indolium-2-yl]-2,4,6-heptatrien-1-ylidene}-1,1-dimethyl-1,2-dihydro-3H-benzo[e]indol-3-yl]-1-butanesulfonate); IR-775 (2-[2-[2-Chloro-3-[2-(1,3-dihydro-1,3,3-trimethyl-2H-indol-2-ylidene)-ethylidene]-1-cyclohexen-1-yl]-ethenyl]-1,3,3-trimethyl-3H-indolium); IR-780 (2-[2-[2-Chloro-3-[(1,3-dihydro-3,3-dimethyl-1-propyl-2H-indol-2-ylidene) ethylidene]-1-cyclohexen-1-yl]ethenyl]-3,3-dimethyl-1-propylindolium); IR-783 (2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium); IR-806 (2-[2-[2-chloro-3-[2-[1,3-dihydro-3,3-dimethyl-1-(4-sulfobutyl)-2H-indol-2-ylidene]-ethylidene]-1-cyclopenten-1-yl]-ethenyl]-3,3-dimethyl-1-(4-sulfobutyl)-3H-indolium); and/or IR-820 (2-[2-[2-Chloro-3-[[1,3-dihydro-1,1-dimethyl-3-(4-sulfobutyl)-2H-benzo[e]indol-2-ylidene]-ethylidene]-1-cyclohexen-1-yl]-ethenyl]-1,1-dimethyl-3-(4-sulfobutyl)-1H-benzo[e]indolium).

The photochemically active surface molecule may be placed within a distance smaller than the Forster Resonant Excitation Transfer (e.g., 2-10 nm) from a luminescent center. This can be achieved by, e.g., using a sufficiently concentrated layer of active surface molecules, as shown on FIG. 9C.

As seen in FIG. 1A, a spin-labeled antagonist molecule 140 (such as an antagonist with a nitric oxide spin label) is attached (here, via linker 144) to the binding domain 130. No analyte molecule is present. Due to the proximity of the spin-label of the antagonist molecule to the NV center, there is dipole coupling 160 of the spin 142 of the antagonist molecule 140 and the spin 122 of the luminescent center 120, a strong magnetic interaction, resulting in a large splitting in the optically detected EPR spectrum.

As seen in FIG. 1B, the detection system 100 is shown after the attachment of an analyte molecule 150. The analyte molecule displaces the spin-labeled antagonist 140, significantly reducing the spin-spin magnetic interaction (in FIG. 1B, no dipole coupling is shown), and causing the reduction of the splitting in the optically detected EPR spectrum. As seen in FIG. 1B, when an analyte is present, spin-dependent optical emissions 180 are detectable. In some embodiments, what will be detected is a change in its intensity, spectral content, polarization, or combination thereof.

In various aspects, a system may be provided. Referring to FIG. 2, the system 200 may include a plurality of nanometer scale analyte specific sensors 100 as disclosed herein, positioned within a fluid 210 containing a molecule of interest 220. The system may also include a light source 230 configured to illuminate the plurality of nanometer scale analyte specific sensors with at least one wavelength of light 232 that a luminescent center 120 of each nanometer scale analyte specific sensors is capable of absorbing. The system may also include an additional source 234 of radiofrequency illumination 236. The system may also include an external constant magnetic field 280. In some embodiments, the fluid may be disposed within a container 212. In some embodiments, the fluid may be, e.g., flowing in a pipe, tube, or channel. Container, pipe, tube, or channel may include a window 214 through which the at least one wavelength of light can pass through to the sensors.

In some embodiments, emissions from the sensor(s) may be detected by a detector 240, such as a photodetector. The detector may be operably coupled to one or more processors 250, which may be operably coupled to the light source 230. As will be understood by those of skill in the art, the one or more processors may be couple to memory, non-transitory computer readable storage devices, input/output devices (displays, keyboards, etc.), switches, knobs, etc., for allowing a user to control the system and receive feedback from the system.

In various aspects, a kit may be provided. The kit may include a plurality of nanometer scale analyte specific sensors as disclosed herein, and may include a light source adapted to illuminate the plurality of nanometer scale analyte specific sensors with at least one wavelength of light a luminescent center of each nanometer scale analyte specific sensors is capable of absorbing.

In various aspects, a method for detecting an analyte may be provided. Referring to FIG. 3, the method 300 may include placing 310 a nanometer scale analyte specific sensor as disclosed herein in a fluid containing a molecule of interest. See, e.g., FIG. 2. The method may include exciting 320 photoprotective groups of the photochemically active molecules, by photoexciting 322 the luminescent center using at least one wavelength of light and causing 324 the luminescent center to undergo Forster Resonant Excitation Transfer (FRET) to an optical chromophore of a photoprotective group. The method may include allowing 330 the excited photoprotective groups to dissociate, leaving a functional group sterically available. The method may include attaching 340 the molecule of interest to the sterically available functional group.

In various aspects, a method for producing a nanometer scale analyte specific sensor may be provided. Referring to FIG. 4, the method 400 may include providing 410 a first material (such as diamond) having a luminescent center (such as an NV center) within predetermined distance (such as 2-5 nm) of a first surface. The luminescent center may be configured to emit within an optical emission range. The method may include providing 420 photochemically active molecules, where an optical absorption range of the photochemically active molecules at least partially overlaps the optical emission range. The method may include coating 430 the first surface of the first material with the photochemically active molecules. The photochemically active molecules may include a photo-uncaging protective group (such as a group based on a near-IR cyanine dye). Coating the first surface may include depositing 432 a monolayer containing the photo-uncaging protective group.

Positionally precise functionalization of the surface brings the spin-based sensor into the vicinity of the buried NV center. There is no chemical information on the surface of the diamond to indicate the presence of the NV center. In sensing applications, one needs to place the analyte molecule within ~5 nm of the NV center to enable the detection. In single-molecule NMR experiments, the positioning requirements are even higher due to the weakness of nuclear-electron spin coupling.

Conventionally, there are two methods of surface positioning, both are not satisfactory. In the first (stochastic), the sample is spread uniformly over the surface and if the density is high enough, then the molecule of interest will be near the NV center. This approach suffers from low sensitivity as most analyte molecules are bound to sensing domains that are too far away from NV centers. Another approach is to use scanning microscopy to locate the NV center and then attempt to place a molecule of interest in its vicinity. This approach is not scalable and suffers from poor positioning accuracy.

Disclosed is an alternative approach that is based on the combination of photochemical uncaging of surface-bound protective groups and Forster Resonant Energy Transfer (FRET) from the NV center to these groups. The efficiency of the excitation transfer can be determined as a function of the NV center deposition depth, the surface density of the excitation accepting site, and the excitation transfer distance. The disclosed technique is efficient and spatially precise. The FRET-driven process should be contrasted with the emission-absorption process with a former is a coherent coupling through the electromagnetic field. The emission reabsorption process is limited in its accuracy to the wavelength of NV emission and is inefficient due to the low optical density of the absorbing media. FRET drive process is free of these shortcomings due to the much stronger dipole-dipole coupling with a donor-acceptor coupling efficiency approaching 100% given a short distance between them.

The suggested functionalization processes can be accomplished through several routes such as FRET-driven deprotection of surface-bound photolabile groups (See FIGS. 5A-5F) and a FRET-driven excitation of photoinitiator in a photoresist (See FIG. 6). As an additional route and FRET-driven photoredox catalyzed surface chemistry can be utilized, but the diffusion transport of the redox reaction might limit the spatial resolution of the functionalization.

The first suggested approach contains four basic steps. In the first step of the deposition process, shown in FIG. 5A, the surface of the diamond sample 110 is covered with a monolayer 170, containing the photo-uncaging protective group 174 (i.e. the functional group that dissociates under the photoexcitation). Such a process can be accomplished utilizing the UV grafting of CVD grown isotopically pure diamond, e.g., via attachment of an amine functional group. Another route to couple the functional groups to the diamond surface is through the use of carboxylic groups on the diamond surface. To activate the surface carboxylic groups a water-soluble mixture of 1-ethyl-3-(3-dimethylamino)propyl)carbodiimide (EDC) and/or a N-hydroxy-sulfosuccinimide (NETS) can be used. Non-covalent, physisorbed coatings are also possible, although they do not provide the resilience, expected from detection systems. The photoprotected caged group 172 can be attached to the surface first, and the protective photosensitive group 174 can be attached later. The absorption spectrum of such a photoprotective group may lay in, e.g., the red to the near-IR portion of the spectrum. The absorption spectrum of the photoprotective group may overlap, and preferably strongly overlaps, with the emission spectrum of the NV-center. The term "strongly overlaps" indicates at least 30%, at least 40%, at least 50%, at least 60%, at least 70%, at least 80%, at least 90%, or at least 95% of the wavelengths of the emission spectrum of the NV-center is absorbed by the photoprotective group.

Examples of such a photo-uncaging group can be found in Gorka, et al., "A Near-IR Uncaging Strategy Based on Cyanine Photochemistry", J Am Chem Soc. 2014 Oct. 8; 136(40): 14153-14159, the contents of which are incorporated by reference herein in its entirety, and is based on a near-IR cyanine dye.

At the second step, shown in FIG. 5B, the sample is illuminated with optical radiation 510, within the region of NV center absorption (from 450 nm to 600 nm). Once photoexcited, the NV center undergoes Forster Resonant Excitation Transfer (FRET) 512 to the optical chromophore of the photoprotective group. FRET transfer is a very short range (~4 nm, typically, but may be 2-10 nm, or 2-5 nm) and is highly efficient within that range. At the third step, shown in FIG. 5C, the excited protective groups dissociate, leaving the functional group sterically available 520 (which was previously caged) for the attachment process. In the fourth step, shown in FIG. 5D, the available functional groups 520 attach the molecule of interest 530 such as a spin-labeled antibody.

FIGS. 5E and 5F show a more detailed example, where photoprotective groups 174 based on the dissociating near-IR cyanine dye are operably coupled to the device, but after irradiation (in this example, via exposure to 690 nm wavelengths), the protective group dissociates, leaving the functional group available for attachment.

The second suggested route is illustrated in FIG. 6. This route provides a colocalization of the luminescent center with surface-bound functional groups through the FRET process to, e.g., a red light-sensitive photoresist 605. The photoresist is the polymer system that can provide exceeding thin coatings down to few nanometers. The photoresist contains a light-absorbing photoinitiator molecule 607 that controls the initiation of the polymerization. The photoinitiator serves as an acceptor of the FRET excitation transfer process with a donor being the luminescent center.

As seen in FIG. 3, a first step 610 for positionally accurate functionalization through excitation transfer to the red light-sensitive photoinitiator of the photoresist includes optical excitation 510 of the luminescent center 120, and excitation transfer 512 to the photoinitiator 607 of the photoresist 605. The second step 620 includes either removal of the exposed positive photoresist (left) or removal of the unexposed negative photoresist (right). The third step 630 includes functionalization of the exposed substrate surface (left) or functionalization of the remaining photoresist (right).

The efficiency of the attachment process and the spatial distribution of attachment sites can be analyzed. In this example, the first process (see FIGS. 5A-5D) is considered. The spectral properties of near-IR photo uncaging groups based on cyanine dyes will be utilized in the analysis.

Utilizing the emission spectrum of the NV center and the absorption spectrum of IR-780 based functional group (see FIG. 7), the excitation transfer distance is given by:

$$R_0^6 = \frac{9000(\ln 10)k^2 Q_D}{N_A 128\pi^5 n^4} \cdot \frac{\int_0^\infty \varepsilon(v)F_D(v)v^4 dv}{\int_0^\infty F_D(v)dv} . \tag{1}$$

Given the refractive index of diamond of 2.4, the FRET distance is 4.3 nm. The relative geometry of the NV center with acceptor sites is illustrated in FIG. 8.

The optical excitation is transferred from a single luminescent center to the distribution of acceptors on the surface. The excitation of the donor is transmitted to a collection of acceptors with random distributions of positions. The evolution donor excited state probability for a given distribution of acceptors $P_{ex}$ is given by.

$$\frac{dP_{ex}}{dt} = -\left(\frac{1}{\tau_{DL}} + \sum_{i-1}^{N} k_f(x_i, y_i)\right)P_{ex}. \tag{2}$$

Where $\tau_{DL}$ is the excited state lifetime of the donor molecule and $k_f(x_i, y_i)$ is the excitation transfer rate from donor to acceptor at $(x_i, y_i)$.

$$k_f(x_i, y_i) = \frac{1}{\tau_{DL}} \frac{R_0^6}{\left(d^2 + x_i^2 + y_i^2\right)^3} . \tag{3}$$

Once the excitation is transmitted to the acceptor molecules it can either dissipate or cause the dissociation of the protective group. The evolution of the acceptor molecule i at the position $(x_i, y_i)$ is described by the following equation.

$$\frac{dP_{ET}^i}{dt} = -\left(\frac{1}{\tau_{AL}} + k_D\right)P_{ET}^i + k_f(x_i, y_i)P_{ex}. \tag{4}$$

Where $\tau_{AL}$ is the excited state lifetime of the acceptor molecule, $k_D$ is the rate of dissociation (uncaging). The evolution of Eq (2) for P depends on the random spatial distribution of acceptors. The averaged thermodynamic limit of excited-state evolution is given by $$P_{ex}(t) = \exp\left(-\frac{t}{\tau_{DL}}\right)\exp\left(-2\pi C \int_0^\infty [1 - S(t, r)]r dr\right) \tag{5}$$

where $S(t, r)$ is the survival probability of a single donor in the presence of a single acceptor pair, C is the acceptor surface concentration.

$$S(t, r) = \exp\left(\frac{t}{\tau_{DL}} \frac{R_0^6}{\left(d^2 + r^2\right)^3}\right) \tag{6}$$

The survival probability of the donor excited state after some simple rearrangements:

$$P_{ex}(t) = \exp\left(-\frac{t}{\tau}\right)\exp\left(-\pi Cd^2 \int_0^\infty \left[1 - \exp\left(\frac{t}{\tau_L}\left(\frac{R_0}{d}\right)^6 \frac{1}{(1+y)^3}\right)\right]dy\right) \tag{7}$$

Consider the behavior of the "form factor" integral $$f(\alpha) = \int_0^\infty \left[1 - \exp\left(\alpha \frac{1}{(1+y)^3}\right)\right]dy, \ \alpha = \frac{t}{\tau_L}\left(\frac{R_0}{d}\right)^6 \tag{8}$$

11

The plot of the function $f(\alpha)$ is shown in FIG. 9A. This function allows one to compute the decay of the donor excited state population for the entire range of the concentrations. The decay of the excited state population of the NV center in the presence of different concentrations of surface acceptors is shown in FIG. 9B. Nitrogen vacancy excited state lifetime $\tau_L=23$ ns, the deposition depth is 3 nm. It is easy to see that the presence of the surface acceptor groups rapidly reduces the excited state lifetime and the quantum yield of NV center luminescence. The reduction in the emission is due to the appearance of the excitation transfer channel, and it can be used to quantify its efficiency. From the numerical analysis, it follows that for the photo-uncaging group, described previously, and NV center deposited at 3 nm depth, 50% chance of excitation transfer is at the surface acceptor density 0.02 groups/nm$^2$ for deposition depth of 5 nm, the surface density is 0.07 groups/nm$^2$; for 10 nm is at 1 acceptor/nm$^2$. FIG. 9C shows the quantum yield of the excitation transfer to surface uncaging groups as a function of acceptor concentrations for different NV center deposition depths. It is easy to see that even for the largest deposition depths, there is an appreciable probability of excitation transfer to surface groups.

The statistical characteristics of the surface distribution of available binding sites once the photouncaging group dissociated following the optical excitation may be evaluated. Using Eq. (4) for given acceptor site i, one obtains the following probability of excitation $$P_{ET}^i = k_f(x_i, y_i) \int_0^\tau P_{ex}(t_1) \exp\left(-\left(\frac{1}{\tau_{AL}} + k_D\right)(t - t_1)\right) dt_1 \quad (9)$$

The important property of Eq. (9) is that the spatial and temporal dependences of the probability factorize, and all the acceptor sites have identical time evolution of un-caging probability. Thus, the spatial distribution of the attachment probability is proportional to ~$k_f(x,y)$. The properly normalized probability distribution of the attachment sites is then given by Eq (10). The probability distribution is illustrated in FIG. 10A.

$$\rho(r) = \frac{2d^4}{\pi} \frac{1}{(d^2 + r^2)^3} \quad (10)$$

The dispersion of distances of the accepting cites from the origin is given by $$\langle r^2 \rangle = \int_0^\infty \rho(r) r^2 \pi r dr = \int_0^\infty \frac{4d^4}{\pi} \frac{1}{(d^2 + r^2)^3} r^2 \pi r dr = d^2 \quad (11)$$

The distribution of distances, given by Eq. (10) provides a statistical description of the geometric ensemble of the sensing region attachment in the vicinity of the reporting NV-center and allows us to assess sensor performance, its Receiver Operating Curve (ROC curve).

Chemical and Biological Sensor Based on Optically Detected Electron Spin Resonance.

Now, as the statistical description of the ensemble of possible attachment geometries has been obtained, one can analyze the statistical properties of spin-based detectors, illustrated in FIGS. 1A and 1B. The distribution of the sensing site positions around the NV center creates a distribution of spin-spin couplings and consequently the distribution of possible EPR spectra.

The Hamiltonian of the NV center is given by $$\hat{H}_{NV} = \hbar D\left[\hat{S}_z^2 - \frac{2}{3}\right] + \hbar\gamma\vec{B}\cdot\vec{S} \quad (12)$$

Where $\vec{S}$ are the spin operators, D is the "zero-field split" parameter, equal to 2.87 GHz, $\vec{B}$ is the external magnetic field, and $\gamma$ is the electron's gyromagnetic ratio. Once coupled to the external spin ½ label based sensor, the overall spin Hamiltonian becomes $$\hat{H}_{NV-s} = \left(\hbar D\left[\hat{S}_z^2 - \frac{2}{3}\right] + \hbar\gamma\vec{B}\cdot\vec{S}\right)_{NV} \otimes 1_s + \quad (13)$$

$$1_{NV} \otimes \hbar\gamma\vec{B}\cdot\vec{\sigma} + g^2\beta^2\left[\frac{\hat{S}\cdot\hat{\sigma}}{r^3} - \frac{3(\hat{S}\cdot\hat{r})(\hat{\sigma}\cdot\hat{r})}{r^5}\right]$$

Where $\hat{\sigma}$ is the spin operator of the label, $\bar{r}$ is the radius vector from the NV center to the spin-label. $g^2\beta^2$ determines the scale of the magnetic coupling between the NV center and the spin-label, its numerical value is h 0.33 GHz. The attachment of the analyte molecule to the sensor will displace the spin-labeled antagonist molecule. The initial spin-labeled attached configuration and the final spin-labeled displaced by the analyte are distinct random spatial distribution. In both configurations the spin-label occupies a certain volume of the configuration space (position and orientation) and undergoes a diffusion which can result in complex modification of line shapes such as motional narrowing, potentially significantly improving the resolution of the ESR measurement. To incorporate the effect of diffusion and steric limitations on all possible configurations, a complex molecular dynamic simulation coupled to the spin dynamics is required.

Referring to FIG. 10B, one can estimate the performance of the sensor by neglecting the effect of diffusional motion at each step of the ESR measurement and assume that positions of the spin-label are fixed within a sphere of uncertainty in both sensor inactive (analyte unattached 1103) and sensor active (analyte attached 1104) configurations. Additional detection uncertainty is introduced by the precise position of the attachment of the sensor to the diamond surface 1102 relative to the luminescent center 120 with a distribution of distances given by Equation (10).

Every random spatial configuration of the NV-center and the spin-label is generated by the random attachment point with probability density given by Equation (10) and the uniform random distribution of the spin-label within the sphere of uncertainty. One can assume that the detection parameter that separates the sensor ON and OFF states are the heights of the spin-label above the diamond surface. For every configuration from the random set of possible configurations, the energy splitting $\Delta E$ between transitions $m_{S=0}\rightarrow m_{S=+1}$ and $m_{S=0}\rightarrow m_{S=-1}$ is calculated. Such a parameter serves as a sensitive measure for NV-center—spin-label coupling and will indicate the geometry and consequently the state of the sensor. The ensemble of geometries will then induce a probability distribution function of $\Delta E$. The variation of the probability distribution of $\Delta E$ with the height of the spin-label above the diamond surface (or with other variation of the geometry and dynamics) forms the basis of the detection and allows us to compute the statistical characteristics of the detection system (receiver operating characteristic, ROC curve).

The change in the probability density function with the sensor-surface separation is shown in FIGS. 11A-11B. The further the separation of the spin-label from the surface, the smaller is the energy separation. One can notice the spiking of the probability density function around zero energy, corresponding to configurations with the largest separation from NV center to spin-label, occupying a large portion of the state space. There is also a sharp cut-off in the region of high interaction, corresponding to the configuration of the closest approach of the NV center and sensing domain.

Once the statistical description of the measurement is obtained, the ROC curve can be obtained. One can assume that the state sensor OFF corresponds to the position of 1 nm above the surface. The ROC curves for the several ON positions of the sensor are shown in FIGS. 12 and 13. As expected, the performance of the sensor is improved with higher geometric contrast of ON and OFF states. It should be noted that the sensor exhibits a very low False Positive/Alarm Rate and an appreciable probability of detection.

The performance of the sensor is significantly improved if the deposition depth is shallow as it offers stronger coupling to the spin-label and higher contrast in the energy difference variation. FIG. 13 illustrates the ROC curves for three different deposition depths.

Various modifications may be made to the systems, methods, apparatus, mechanisms, techniques and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof. As such, the appropriate scope of the invention is to be determined according to the claims.

What is claimed is:

1. A method for placing a chemical sensitive moiety in a close proximity of a luminescent center, comprising:

placing a nanometer scale analyte specific sensor in a fluid containing a molecule of interest, the nanometer scale analyte specific sensor comprising a first material having a luminescent center within predetermined distance of a first surface coated with photochemically active molecules, where the luminescent center configured to emit within an optical emission range, and an optical absorption range of the photochemically active molecules at least partially overlaps the optical emission range;

exciting photoprotective groups of the photochemically active molecules, by photoexciting the luminescent center using at least one wavelength of light and causing the luminescent center to undergo Forster Resonant Excitation Transfer (FRET) to an optical chromophore of a photoprotective group;

allowing the excited photoprotective groups to dissociate, leaving a functional group sterically available; and attaching the molecule of interest to the sterically available functional group.

2. The method according to claim 1, wherein the first material is a diamond, silicon carbide, gallium nitride, aluminum nitride, or hexagonal-boron nitride.

3. The method according to claim 2, wherein the diamond includes an nitrogen vacancy (NV) center in diamond, a silicon vacancy (SiV) center in diamond, or a carbon anti-site-vacancy pair in silicon carbide.

4. The method according to claim 1, wherein the predetermined distance is 2-5 nanometers.

5. The method according to claim 1, wherein the photochemically active molecules include a photo-uncaging protective group, and wherein coating the first surface comprises depositing a monolayer containing the photo-uncaging protective group.

6. The method according to claim 5, wherein the photo-uncaging protective group is based on near-IR cyanine dye.

* * * * *